United States Patent
Hansen et al.

(10) Patent No.: US 9,035,031 B2
(45) Date of Patent: May 19, 2015

(54) METHOD FOR PROVIDING A β-LACTOGLOBULIN PRODUCT AND AN α-ENRICHED WHEY PROTEIN ISOLATE

(75) Inventors: Marie Bendix Hansen, Frederiksberg (DK); Allan Otto Fog Lihme, Birkerød (DK); Malene Fog Lihme, Vordingborg (DK)

(73) Assignee: UPFRONT CHROMATOGRAPHY A/S, Copenhagen O (DK)

( * ) Notice: Subject to any disclaimer, the term of this patent is extended or adjusted under 35 U.S.C. 154(b) by 777 days.

(21) Appl. No.: 13/063,579

(22) PCT Filed: Sep. 29, 2009

(86) PCT No.: PCT/EP2009/062602
§ 371 (c)(1),
(2), (4) Date: May 25, 2011

(87) PCT Pub. No.: WO2010/037736
PCT Pub. Date: Apr. 8, 2010

(65) Prior Publication Data
US 2011/0218327 A1  Sep. 8, 2011

(30) Foreign Application Priority Data
Sep. 30, 2008  (DK) .................................. 200801369

(51) Int. Cl.
*A23J 1/00*  (2006.01)
*A23L 1/305*  (2006.01)
*C07K 1/18*  (2006.01)
*A23C 21/06*  (2006.01)
*A23J 1/20*  (2006.01)

(52) U.S. Cl.
CPC ................. *A23L 1/3056* (2013.01); *C07K 1/18* (2013.01); *A23C 21/06* (2013.01); *A23J 1/205* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,420,249 A | 5/1995 | de Wit et al. | |
| 5,756,680 A | 5/1998 | Ahmed et al. | |
| 5,968,586 A | 10/1999 | Etzel | |
| 5,986,063 A | 11/1999 | Etzel | |
| 6,096,870 A | 8/2000 | Mozaffar et al. | |
| 2006/0160212 A1* | 7/2006 | Manickavasagam | ......... 435/325 |
| 2007/0092960 A1 | 4/2007 | Hansen et al. | |
| 2008/0182979 A1 | 7/2008 | Lihme et al. | |

FOREIGN PATENT DOCUMENTS

| | | |
|---|---|---|
| EP | 0 538 350 | 4/1993 |
| WO | WO 92/00799 | 1/1992 |
| WO | WO 92/18237 | 10/1992 |
| WO | WO 95/19714 | 7/1995 |
| WO | WO 97/17132 | 5/1997 |
| WO | WO 98/08603 | 3/1998 |
| WO | WO 98/33572 | 8/1998 |
| WO | WO 00/57982 | 10/2000 |

OTHER PUBLICATIONS

Anspach et al. "Expanded-bed chromatography in primary protein purification" J. Chromatography A, 865 (1999) 129-144.*
Amersahm Biosciences bulletin 18-1132-29, "Protein Purification Handbook" pp. 1-95.*
International Search Report for corresponding International Application No. PCT/EP2009/062602.

* cited by examiner

*Primary Examiner* — Daniel E Kolker
*Assistant Examiner* — James Rogers
(74) *Attorney, Agent, or Firm* — Merchant & Gould P.C.

(57) ABSTRACT

The present invention relates to isolation of whey proteins and the preparation of a whey product and a whey isolate. In particular the present invention relates to the isolation of a β-lactoglobulin product and the isolation of an α-enriched whey protein isolate from whey obtained from an animal. The α-enriched whey protein isolate provided by the present invention is besides from being low in β-lactoglobulin also high in α-lactalbumin and immunoglobulin G.

7 Claims, 1 Drawing Sheet

METHOD FOR PROVIDING A β-LACTOGLOBULIN PRODUCT AND AN α-ENRICHED WHEY PROTEIN ISOLATE

This application is a National Stage Application of PCT/EP2009/062602, filed 29 Sep. 2009, which claims benefit of Serial No. PA 2008 01369, filed 30 Sep. 2008 in Denmark and which applications are incorporated herein by reference. To the extent appropriate, a claim of priority is made to each of the above disclosed applications.

TECHNICAL FIELD OF THE INVENTION

The present invention relates to isolation of whey proteins and the preparation of a whey product and a whey isolate. In particular the present invention relates to the isolation of a β-lactoglobulin product and the isolation of an α-enriched whey protein isolate from whey obtained from an animal.

BACKGROUND OF THE INVENTION

Whey comprises a variety of proteins—two of which are α-lactalbumin and β-lactoglobulin. α-lactalbumin is a protein found in the milk of mammals. However, it represents a major protein in human milk where 40% of the whey proteins are α-lactalbumin. Whey from human milk contains in addition to α-lactalbumin other vital substances such as lactoferrin, immunoglobulins, albumin, enzymes, growth factors, and hormones. β-lactoglobulin does not occur in human milk, but is a characteristic protein in bovine milk.

Due to the large differences in the protein composition of bovine milk and human milk, some infants show different degrees of intolerance to bovine milk and food formulas consisting thereof. Accordingly, α-lactalbumin is largely used both in preparation of humanized milk and compositions of non-allergenic milk products for infants who are allergic to β-lactoglobulin.

Accordingly, it is generally of interest to mimic human milk and the challenge of producing infant formulas is therefore based on the differences seen in the composition of e.g. bovine milk and human milk. To provide infant formulas that mimic human breast milk it is of interest to fractionate bovine whey proteins resulting in a whey protein isolate suitable for infant formulas.

In previously described methods for providing such whey protein isolates whey proteins are often eluted in separate fractions or eluted in such a way that unwanted proteins remains in the whey protein isolate causing the concentration of the interesting and relevant proteins in the whey protein isolate to be reduced.

Traditionally, these disadvantages are solved by either adding specific compounds, originally present in the whey, to whey protein isolate and/or adding additional purification steps to the process. Regarding infant formulas such specific compounds may be immunoglobulin G which is assumed to be of major importance in the development of infant immune defence.

U.S. Pat. No. 5,756,680 (Sepragen Corporation) discloses a method for the sequential separation of whey proteins using radial-flow chromatography. The method separates at least five different proteins; immunoglobulin G and β-lactoglobulin, α-lactalbumin, bovine serum albumin and lactoferrin from whey.

Thus, it is of interest to provide a method applicable for large-scale production for industrial provision of a β-lactoglobulin product and an α-enriched whey protein isolate from whey in a simple process without or with a limited need for subsequent addition of specific compounds and/or further purification steps.

SUMMARY OF THE INVENTION

The inventors of the present invention surprisingly discovered a method for large-scale production and isolation of a β-lactoglobulin product and an α-enriched whey protein isolate from whey, both of which are of high value. Besides from being low in β-lactoglobulin, the α-enriched whey protein isolate provided by the present invention is also high in α-lactalbumin and immunoglobulin G.

Accordingly, one aspect of the present invention relates to a method for providing a β-lactoglobulin product and an α-enriched whey protein isolate from whey, the method comprises the steps of (i) providing whey obtained from an animal, (ii) adjusting the pH value of the whey to pH 4.5 or below, (iii) loading the whey to a chromatographic support, (iv) optionally washing the chromatographic support using a wash buffer and obtaining a wash fraction, (v) eluting the β-lactoglobulin product from the chromatographic support using a first elution buffer, said first elution buffer having a pH of 4 or less and a salt concentration of at least 0.1M and (vi) eluting the α-enriched whey protein isolate with a second elution buffer.

Other aspects of the present invention relate to a β-lactoglubulin product comprising β-lactoglubulin and the use of said β-lactoglubulin product as a food ingredient. Related aspects pertain to the provision of food ingredients and food products comprising the β-lactoglubulin product.

In a further aspect the present invention relates to a method for purifying the β-lactoglubulin product in order to obtain a composition comprising at least 85% β-lactoglubulin when compared to the amount of proteins in the β-lactoglubulin product.

In further aspects the present invention pertains to an α-enriched whey protein isolate comprising α-lactalbumin and immunoglobulin G and use of said α-enriched whey protein isolate as a food ingredient and/or in an infant formula. Other related aspects pertain to the provision of food ingredients, food products and infant formulas comprising the α-enriched whey protein isolate In a further aspect the present invention relates to a method for improving the isolation of a β-lactoglobulin product and an α-enriched whey protein isolate from whey, the method comprises a first elution conditions having the first specific relation between pH, ionic strength and temperature obtaining the β-lactoglobulin product and a second elution obtaining the α-enriched whey protein isolate.

The present invention will now be described in more detail in the following.

DETAILED DESCRIPTION OF THE INVENTION

Accordingly, the present invention provides a method suitable for large-scale production of both a β-lactoglobulin product and an α-enriched whey protein isolate from whey in a simple and industrial applicable isolation process.

Thus, one aspect of the present invention relates to a method for providing a β-lactoglobulin product and an α-enriched whey protein isolate from whey, the method comprises the steps of (i) providing whey obtained from an animal, (ii) adjusting the pH value of the whey to pH 4.5 or below, (iii) loading the whey to a chromatographic support, (iv) optionally washing the chromatographic support using a wash buffer and obtaining a wash fraction, (v) eluting the β-lactoglobulin product from the chromatographic support using a first elution buffer, said first elution buffer having a pH of 5 or less and a salt concentration of at least 0.1M and (vi) eluting the α-enriched whey protein isolate with a second elution buffer.

Whey

According to the teaching of the present invention the method for providing a β-lactoglobulin product and an α-enriched whey protein isolate from whey comprises the step of:

(i) providing whey obtained from an animal

The method according to the present invention may preferably be targeted for industrial large-scale fractionation processes where large volumes of whey must be handled.

As the present invention is targeted for industrial large-scale fractionation processes it may be preferred that the animal from which the whey is obtained may be an animal traditionally used for large-scale milk production. Preferably, the animal from which the whey is obtained may be selected from the group consisting of cow, buffalo, sheep, goat and camel. However, animals not traditionally used for large-scale milk production may also be applied in respect of the present invention.

As the present invention aims at fractionating whey proteins, such as β-lactoglobulin and α-lactalbumin, by fractionation processes using pH values below 4.5, it may be preferred that the whey used according to the present invention may be a non-casein containing milk product. Caseins tend to coagulate at low pH and may thus cause interference in the fractionation process.

In the present context the term "protein" relates to a compound of biological origin comprising at least two amino acids, such as peptide, polypeptide, lipoprotein, lipopolypeptide, glycopeptides, glycoprotein, enzyme, antibody and immunoglobulin.

In the present context, the term "non-casein containing milk products" relates to milk and other milk derived raw materials, such as whey, comprising no casein.

In an embodiment of the present invention the non-casein containing milk products comprise less than 2 mg casein/L whey, e.g. less than 1 mg casein/L whey, such as less than 0.5 mg casein/L whey.

The fractionation processes differs in their sensitivity to coagulated casein, thus in some fractionation processes processed milk derived raw materials comprising casein or coagulated casein may be applied.

In the dairy industry non-casein containing milk products are traditionally obtained from cheese production, however non-casein containing milk products obtained from other processes may also be applied. Accordingly, the non-casein containing milk products may be selected from the group consisting of sweet whey, acidic whey, ideal whey, demineralised whey, nano-filtered whey, ultra filtered whey and macro filtered milk (see examples 1 and 7).

pH Adjustment

According to the teaching of the present invention the method for providing a β-lactoglobulin product and an α-enriched whey protein isolate from whey further comprises the step of:

(ii) adjusting the pH value of the whey to pH 4.5 or below

Prior to being applied to the chromatographic support the pH of the whey may be adjusted depending on e.g. the ligand chemistry and the type of whey provided.

In a preferred embodiment of the present invention pH value of the whey may be adjusted to a pH facilitating optimal adsorption or other type of fixation of the proteins of interest in the whey. Such proteins of interest include but are not limited to β-lactoglobulin, α-lactalbumin, immunoglobulin G, lactoferrin and bovine serum albumin. In the present invention the pH value of the whey is adjusted to pH of 5 or below, such as 4.5 or below, e.g. pH 4.0 or below, such as pH 3.5 or below, e.g. pH 3.0 or below, such as pH 2.5 or below (see example 1)

As the present invention aims at large-scale fractionation and isolation it may be preferable to use a low cost mineral acid such as hydrochloric acid, phosphoric acid, sulphuric acid to adjust the pH value of the whey. However, food grade organic acids such as acetic, citric and lactic acid may be particularly preferred.

Alternatively, the pH value of the whey may be adjusted by passing the whey through a strong cation exchanger (acidic form). The cation exchanger will bind salts from the whey and release $H^+$-ions and thereby decrease pH to the desired value. In a preferred embodiment the cation exchanger may be selected from the group consisting of cation exchangers normally used for de-ionising of e.g. water and whey such as Amberlite IR 120, Amberlyst 15, Dowex 50WX8.

In order to facilitate optimal adsorption or fixation of the proteins of interest to the chromatographic support, to provide a β-lactoglobulin product and an α-enriched whey protein isolate, it may be preferred that the whey has a temperature in the range from 1-65° C., such as in the range from 5-60° C., e.g. in the range from 10-55° C., such as in the range from 15-50° C., e.g. in the range from 20-45° C., such as in the range from 25-40° C., e.g. in the range from 30-35° C., such as in the range from 20-35° C., e.g. in the range from 20-30° C. (see examples 2 and 10).

Chromatographic Support

According to the teaching of the present invention the method for providing a β-lactoglobulin product and an α-enriched whey protein isolate from whey further comprises the step of:

(iii) loading the whey to a chromatographic support

The chromatographic support to be used may be any kind suitable for either Expanded Bed Adsorption (EBA) or suitable for packed bed adsorption or a combination thereof. The chromatographic support may be used in either a batch system or in a continuous system. In the present context the term "chromatographic support" relates to any kind of container comprising an adsorbent and which can be supplied with at least one inlet for the application of the whey to the column and at least one outlet to elute the proteins of interest.

The fact that the EBA technology generally can work efficiently with non-clarified raw materials makes it attractive to implement for the isolation and fractionation of biomolecular substances, such as proteins from milk and whey. Compared to processes based on packed bed adsorption techniques EBA may offer a robust process comprising fewer steps and thus results in increased yields and an improved process economy. Due to the expansion of the adsorbent bed during execution of an EBA process, EBA columns may further be scaled up to industrial scale without any significant considerations regarding increased back pressures or breakdown of the process due to clogging of the system which is often a problem when using packed bed columns. However, the present state of art within the EBA technology does not adequately address the specific problems associated with the treatment of extremely high volumes of raw materials, such as but not limited to milk and whey.

An object of the invention is to provide a method for providing a β-lactoglobulin product and an α-enriched whey protein isolate from whey based on adsorption to any type of solid phase material of any shape and format. Thus in a preferred embodiment the chromatographic support may be selected from the group consisting of expanded bed adsorption, packed bed adsorption, batch adsorption, suspended bed adsorption, membrane based adsorption an any combination hereof. These chromatographic supports are characterised by the use of selective ligand chemistry enabling the specific binding and subsequent elution of one protein, or alternatively enabling a group specific binding of a few proteins.

General Expansion Bed Adsorption technology is known to the person skilled in the art and the method of the present invention may be adapted to the processes described in, for example, WO 92/00799, WO 92/18237, WO 97/17132, WO 00/57982 and WO 98/33572.

Adsorbent

As stated, it is an overall object of the present invention to provide a novel method for providing a β-lactoglobulin product and an α-enriched whey protein isolate from whey, wherein said method is based on the use of a chromatographic support such as the EBA methodology and EBA adsorbents fulfilling the needs for implementing efficient EBA processes in an industrial scale.

Thus, in one embodiment of the present invention the chromatographic support comprises an adsorbent.

An initial but optional step in the method of the invention typically involves the equilibration of the adsorbent. In a preferred embodiment, the equilibration liquid is a liquid having a pH value of 4.5 or below or equilibration liquid is adjusted to a pH of 4.5 or below, such as 4 or below, e.g. 3.5 or below, such as 3.0 or below, e.g. 2 or below. Such pH adjustment may be performed using the acids or combination of acids previously mentioned.

In the present context the term "adsorbent" relates to the entire bed present in the adsorbent column and the term "adsorbent particle" is used interchangeably with the term "particle" and relates to the individual single particles which makes up the adsorbent.

The flow rate, the size of the particles and the density of the particles all have influence on the expansion of the fluid bed and it is important to control the degree of expansion in such a way to keep the adsorbent particles inside the column. The degree of expansion may be determined as H/H0, where H0 is the height of the bed in packed bed mode and H is the height of the bed in expanded mode. In a preferred embodiment of the present invention the degree of expansion H/H0 is in the range of 1.0-10 e.g. 1.0-6, such as 1.2-5, e.g. 1.3-5, such as 1.5-4, e.g. s 4-6, such as 3-5, e.g. 3-4, such as 4-6.

In an other preferred embodiment of the present invention the degree of expansion H/H0 is at least 1.0, such as at least 1.5, e.g. at least 2, such as at least 2.5, e.g. at least 3, such as at least 3.5, e.g. at least 4, such as at least 4.5, e.g. at least 5, such as at least 5.5, e.g. at least 6, such as at least 10. The density of the EBA adsorbent particle is found to be highly significant for the applicable flow rates in relation to the maximal degree of expansion of the adsorbent bed possible inside a typical EBA column (e.g. H/H0 max 3-5) and must be at least 1.3 g/mL, more preferably at least 1.5 g/mL, still more preferably at least 1.8 g/mL, even more preferably at least 2.0 g/mL, most preferably at least 2.3 g/mL in order to enable a high productivity of the method.

The density of non-porous core material adsorbent is meant to describe the density of the non-porous core material adsorbent in its fully solvated (e.g. hydrated) state as opposed to the density of a dried adsorbent.

In a preferred embodiment of the present invention the adsorbent particle has a mean particle size of at most 200 μm, e.g. at most 180 μm, particularly such as at most 160 μm, e.g. at most 150 μm, such as at most 140 μm, e.g. at most 130 μm, such as at most 120 μm, e.g. at most 110 μm, such as at most 100 μm. even more Typically, the adsorbent particle has a mean particle size in the range of 100-200 μm, such as 120-180 μm, e.g. 140-160.

It is to be understood that mean particle sizes below 100 μm such as below, 90 μm, e.g. below 80 μm, such as below 70 μm, e.g. below 60 μm, such as below 50 μm, e.g. below 40 μm, such as below 30 μm, e.g. below 20 μm, such as below 10 μm are also covered by the present invention. Using adsorbent particles having a mean particle size below 100 μm however leads to lower productivity compared to using adsorbent particles having a mean particle size at or above 100 μm.

The high density of the adsorbent particle may be, to a great extent, achieved by inclusion of a certain proportion of a dense non-porous core materials, preferably having a density of at least 4.0 g/mL, such as at least 10, e.g. at least 16, such as at least 25. Typically, the non-porous core material has a density in the range of about 4.0-25 g/ml, such as about 4.0-20 g/ml, e.g. about 4.0-16 g/mL, such as 12-19 g/ml, e.g. 14-18 g/ml, such as about 6.0-15.0 g/mL, e.g. about 6.0-16 g/ml Subsequently, the whey may be loaded and proteins of interest are adsorbed or fixated to the adsorbent, typically under pressure. Particulate material and soluble impurities are optionally removed from the column during the pH adjusted wash.

The fractionation may be performed efficiently by loading the whey to the adsorbent column at a linear flow rates of at least 3 cm/min, such as at least 5 cm/min, e.g. at least 8 cm/min, such as at least 10 cm/min e.g. 20 cm/min.

Typically the flow rate may be selected in the range of 5-50 cm/min, such as in the range of 5-35 cm/min, e.g. in the range from 5-15 cm/min, such as in the range of 10-30 cm/min, e.g. in the range of 25-50 cm/min.

In an embodiment, the whey may be loaded to the adsorbent column with a linear flow rate of at least 200 cm/hour, such as at least 300 cm/hour, more preferably at least 400 cm/hour, such as at least 500 or 600 cm/hour, such as at least 900 cm/hour.

When the whey may be loaded to the adsorbent column the ratio between the adsorbent particle present in the column and the whey may be optimized in order to retain a high capacity of the adsorbent column and to obtain a high purity of the protein or proteins to be isolated. In a preferred embodiment of the present invention the loading ratio of the whey may be at least 2 g α-lactalbumin/L adsorbent, e.g. at least 4 g α-lactalbumin/L adsorbent, such as at least 5 g α-lactalbumin/L adsorbent, e.g. at least 10 g α-lactalbumin/L adsorbent, such as at least 15 g α-lactalbumin/L adsorbent, e.g. at least 20 g α-lactalbumin/L adsorbent, such as at least 25 g α-lactalbumin/L adsorbent, e.g. at least 30 g α-lactalbumin/L adsorbent As will be apparent to the skilled artisan the protein composition in the whey depends to a large extent on the aminal from which the whey is obtained. Furthermore the protein composition depends on the season during which the whey was obtained as changes in the diet of the animal affect both the composition and the amount of proteins in the whey. Moreover the amount of protein in the whey depends on the dairy method used for prior to obtaining the whey.

Thus, in an embodiment of the present invention, the loading ratio of the whey may be at least 12 g protein/L adsorbent, such as at least 30 g protein/L adsorbent, e.g. at least 60 g protein/L adsorbent, such as at least 90 g protein/L adsorbent, e.g. at least 120 g protein/L adsorbent, such as at least 150 g protein/L adsorbent, e.g. at least 180 g protein/L adsorbent.

The adsorbent particle used according to the invention must be at least partly permeable to the proteins to be isolated in order to ensure a significant binding capacity in contrast to impermeable particles that can only bind the target molecule on its surface resulting in relatively low binding capacity. The adsorbent particle may be of an array of different structures, compositions and shapes.

Thus, the adsorbent particles may be constituted by a number of chemically derivatised porous materials having the necessary density and binding capacity to operate at the given flow rates per se. The particles are either of the conglomerate type, as described in WO 92/00799, having at least two non-porous cores surrounded by a porous material, or of the pellicular type having a single non-porous core surrounded by a porous material.

In the present context the term "conglomerate type" relates to a particle of a particulate material, which comprises beads of core material of different types and sizes, held together by the polymeric base matrix, e.g. a core particle consisting of two or more high density particles held together by surrounding agarose (polymeric base matrix).

In the present context the term "pellicular type" relates to a composite of particles, wherein each particle consists of only one high density core material coated with a layer of the porous polymeric base matrix, e.g. a high density stainless steel bead coated with agarose.

Accordingly the term "at least one high density non-porous core" relates to either a pellicular core, comprising a single high density non-porous particle or it relates to a conglomerate core comprising more that one high density non-porous particle.

The adsorbent particle, as stated, comprises a high density non-porous core with a porous material surrounding the core, and said porous material optionally comprising a ligand at its outer surface.

Thus, in an embodiment of the present invention the adsorbent may comprise one or more ligands with affinity for proteins. Preferably the adsorbent may be used in a technique selected from the group consisting of ion exchange, hydrophobic adsorption, affinity adsorption, mixed mode ligand adsorption, metal chelate adsorption, reversed phase adsorption, and any combination hereof.

In the present context the term "core" relates to the non-porous core particle or core particles present inside the adsorbent particle. The core particle or core particles may be incidental distributed within the porous material and is not limited to be located in the centre of the adsorbent particle.

The non-porous core constitutes typically of at most 50% of the total volume of the adsorbent particle, such as at most 40%, e.g. at most 30%, such as at the most 25%, e.g. at the most 20%, such as at the most 10%, e.g. at the most 5%.

Examples of suitable non-porous core materials are inorganic compounds, metals, heavy metals, elementary non-metals, metal oxides, non metal oxides, metal salts and metal alloys etc., as long as the density criteria above are fulfilled. Examples of such core materials are metal silicates metal borosilicates; ceramics including titanium diboride, titanium carbide, zirconium diboride, zirconium carbide, tungsten carbide, silicon carbide, aluminum nitride, silicon nitride, titanium nitride, yttrium oxide, silicon metal powder, and molybdenum disilide; metal oxides and sulfides, including magnesium, aluminum, titanium, vanadium, chromium, zirconium, hafnium, manganese, iron, cobalt, nickel, copper and silver oxide; non-metal oxides; metal salts, including barium sulfate; metallic elements, including tungsten, zirconium, titanium, hafnium, vanadium, chromium, manganese, iron, cobalt, nickel, indium, copper, silver, gold, palladium, platinum, ruthenium, osmium, rhodium and iridium, and alloys of metallic elements, such as alloys formed between said metallic elements, e.g. stainless steel; crystalline and amorphous forms of carbon, including graphite, carbon black and charcoal. Preferred non-porous core materials are tungsten carbamide, tungsten, steel and titanium beads such as stainless steel beads.

The porous material may be a polymeric base matrix used as a means for covering and keeping multiple (or a single) core materials together and as a means for binding the adsorbing ligand.

The polymeric base matrix may be sought among certain types of natural or synthetic organic polymers, typically selected from i) natural and synthetic polysaccharides and other carbohydrate based polymers, including agar, alginate, carrageenan, guar gum, gum arabic, gum ghatti, gum tragacanth, karaya gum, locust bean gum, xanthan gum, agaroses, celluloses, pectins, mucins, dextrans, starches, heparins, chitosans, hydroxy starches, hydroxypropyl starches, carboxymethyl starches, hydroxyethyl celluloses, hydroxypropyl celluloses, and carboxymethyl celluloses; ii) synthetic organic polymers and monomers resulting in polymers, including acrylic polymers, polyamides, polyimides, polyesters, polyethers, polymeric vinyl compounds, polyalkenes, and substituted derivatives thereof, as well as copolymers comprising more than one such polymer functionally, and substituted derivatives thereof; and iii) mixture thereof.

A preferred group of polymeric base matrices are polysaccharides such as agarose.

From a productivity point of view it is important that the adsorbent is able to bind a high amount of protein per volume unit of the adsorbent. Thus it has been found that it is preferable to apply adsorbents having a polymeric phase (i.e. the permeable backbone where the ligand is positioned and whereto the actual adsorption is taking place) which constitutes at least 50% of the adsorbent particle volume, preferably at least 70%, more preferably at least 80%, more preferably at least 90% and most preferably 95% of the volume of the adsorbent particles.

The particles size analysis performed and referred to throughout the description is based on an computerised image analysis of the bead population giving the number of particles at any given particle diameter in relation to the total number of particles analysed in the specific measurement. Typically the total number of particles analysed will be in the range of 250-500 particles. These particle size data may be transferred into the volume percent represented by each particle size by a routine mathematical transformation of the data, calculating the volume of each bead and relating this to the total volume occupied by all beads counted in the measurement.

The preferred shape of a single adsorbent particle is substantially spherical. The overall shape of the particles is, however, normally not extremely critical, thus, the particles can have other types of rounded shapes, e.g. ellipsoid, droplet and bean forms. However, for certain applications (e.g. when the particles are used in a fluidised bed set-up), it is preferred that at least 95% of the particles are substantially spherical.

Preparation of the particulate material according to the invention may be performed by various methods known per se (e.g. by conventional processes known for the person skilled in the art, see e.g. EP 0 538 350 B1 or WO 97/17132. For example, by block polymerisation of monomers; suspension polymerisation of monomers; block or suspension gelation of gel-forming materials, e.g. by heating and cooling (e.g. of agarose) or by addition of gelation "catalysts" (e.g. adding a suitable metal ion to alginates or carrageenans); block or suspension cross-linking of suitable soluble materials (e.g. cross linking of dextrans, celluloses, or starches or gelatines, or other organic polymers with e.g. epichlorohydrin or divinyl sulphone); formation of silica polymers by acidification of silica solutions (e.g. block or suspension solutions); mixed procedures e.g. polymerisation and gelation; spraying procedures; and fluid bed coating of density controlling particles; cooling emulsions of density controlling particles suspended in polymeric base matrices in heated oil solvents; or by suspending density controlling particles and active substance in a suitable monomer or copolymer solution followed by polymerisation.

In a particularly suitable embodiment generally applicable for the preparation of the particulate material according to the invention, a particulate material comprising agarose as the polymeric base matrix and steel beads as the core material is obtained by heating a mixture of agarose in water (to about 95° C.), adding the steel beads to the mixture and transferring the mixture to a hot oil (e.g. vegetable oils), emulsifying the mixture by vigorous stirring (optionally by adding a conventional emulsifier) and cooling the mixture. It will be appreciated by the person skilled in the art that the particle size (i.e. the amount of polymeric base matrix (here: agarose) which is incorporated in each particle can be adjusted by varying the speed of the mixer and the cooling process. Typically, following the primary production of a particle preparation the particle size distribution may be further defined by sieving and/or fluid bed elutriation.

The porous matrix, such as polymer agarose, is typically chemically derivatised with a low molecular weight compound referred to herein as the ligand and the adsorbent comprises a ligand with affinity to proteins. The ligand constitutes the adsorbing functionality of the adsorbent media or the polymeric backbone of the adsorbent particle has a binding functionality incorporated per se.

In a presently preferred embodiment the ligand may be negatively charged at pH 4.5 or below, such as 3.5 or below, e.g. 3.0 or below, e.g. 2.5 or below.

Well-known ligand chemistries such as cation exchangers, e.g. sulfonic acid carboxylic acid have been proven to be efficient tools for binding of whey proteins. At specific pH-values the proteins are positively charged, and selective interaction with a cation exchanger can be obtained.

Such affinity ligands, like the chargeable moieties, may be linked to the base matrix by methods known to the person skilled in the art, e.g. as described in "Immobilized Affinity Ligand Techniques" by Hermanson et al., Academic Press, Inc., San Diego, 1992. In cases where the polymeric base matrix does not have the properties to function as an active substance, the polymeric base matrix (or matrices where a mixture of polymers are used) may be derivatised to function as an active substance in the procedures of activation or derivatisation. Thus, materials comprising hydroxyl, amino, amide, carboxyl or thiol groups may be activated or derivatised using various activating chemicals, e.g. chemicals such as cyanogen bromide, divinyl sulfone, epichlorohydrin, bisepoxyranes, dibromopropanol, glutaric dialdehyde, carbodi-imides, anhydrides, hydrazines, periodates, benzoquinones, triazines, tosylates, tresylates, and diazonium ions.

Specifically preferred methods for chemical derivatization and specific ligands applicable according to this invention are described in WO 98/08603.

In order to ensure an optimal adsorption strength and productivity of the adsorbent it has been found that the ligand concentration on the adsorbent is very significant. Thus, in a suitable embodiment, the adsorbent carries ligands for adsorption of the proteins of interest in a concentration of 50-200 mmol/L adsorbant, such as in the range from 90-150 mmol/L adsorbant, e.g. in the range from 100-130 mmol/L adsorbant (see example 6).

Preferred ligands may be selected from the group consisting of chemical structures containing sulfonic acid, carboxylic acid or other acidic groups, such as propan sulfonic acid, butan sulfonic acid, chloroacetic acid (see examples 1 and 11).

It may be presently preferred that at least 50%, such as at least 55%, e.g. at least 60%, such as at least 65%, e.g. at least 70%, such as at least 75%, e.g. at least 80%, such as at least 85%, e.g. at least 90%, such as at least 95%, e.g. at least 96%, such as at least 97%, e.g. at least 98%, such as at least 99% of the proteins present in the whey are adsorbed or fixed on the chromatographic support.

This amount of proteins present in the whey being adsorbed or fixed on the chromatographic support may vary, mainly because of the varying content of glycomacropeptide (GMP) in the whey depending on the type of whey, as substantially no GMP bind to the chromatographic support and therefore, may be found in the run-through fraction. In the context of the present invention the term "substantially no GMP bind" relates to at most 2% of the GMP present in the whey bind to the chromatographic support, such as at most 1%, e.g. at most 0.5%, such as at most 0.01% of the GMP present in the whey bind to the chromatographic support.

It may be presently preferred that at least 70%, such as at least 72%, e.g. at least 74%, such as at least 76%, e.g. at least 78%, such as at least 80%, e.g. at least 82%, such as at least 84%, e.g. at least 86%, such as at least 88%, e.g. at least 90%, such as at least 92%, e.g. at least 94%, such as at least 96%, e.g. at least 98%, such as at least 99% of the proteins present in the whey, except glycomacropeptide, are adsorbed or fixed on the chromatographic support.

Based on the above it will be apparent to the skilled person that substantially all proteins in the whey are adsorbed or fixed on the chromatographic support. Thus a run-through fraction is obtained in step (iii). The run-through fraction may comprise impurities such as fat, carbohydrates, minerals and proteins not adsorbed or fixed to the chromatographic support.

If the whey is sweet whey glycomacropeptide (GMP) may be present in the run-through fraction as this particular protein may be negatively or non-charged at pH 4.5 or below.

As GMP is neither desired in the β-lactoglobulin product nor in the α-enriched whey protein product it may be preferred that the run-through fraction obtained in step (iii) and/or the wash fraction obtained in step (iv) comprises at least 90%, such as at least 91%, e.g. at least 92%, such as at least 93%, e.g. at least 94%, such as at least 95%, e.g. at least 96%, such as at least 97%, e.g. at least 98%, such as at least 99% of the glycomacropeptide present in the whey.

Wash

According to the teaching of the present invention the method for providing a β-lactoglobulin product and an α-en riched whey protein isolate from whey further comprises the step of:

(iv) optionally washing the chromatographic support using a wash buffer and obtaining a wash fraction.

Once the whey have been loaded to the chromatographic support, the chromatographic support may be washed using a wash buffer having a value of pH of 5 or below, such as pH 4.5 or below, e.g. pH 4.0 or below, such as pH 3.5 or below, e.g. pH 3.0 or below, such as pH 2.5 or below.

In a preferred embodiment of the present invention the acids applicable for adjusting the pH value of the wash buffer may be selected from the group of acids outlined previously for adjusting the pH value of the whey.

In a particularly interesting embodiment of the invention, the washing and elution of the β-lactoglobulin product may be combined into one step, wherein it is one and the same liquid that is employed for washing out the impurities as well as subsequently eluting the product.

In a preferred embodiment of the present invention the flow rate used for the washing steps may be selected from the ranges outlined previously for loading the whey to the chromatographic support.

In an embodiment of the present invention the run-through fraction obtained in step (iii) and/or washing fraction obtained in step (iv) comprises one or more components selected from the group consisting of, carbohydrate, fat, salt, peptide and protein such as 2 or more, e.g. 3 or more, such as 4 or more of the components. The protein may include glycomacropeptide if the whey is sweet whey. If the chromatographic support is overloaded other proteins may also be present in the run-through fraction.

By applying a wash step, the purity of the β-lactoglobulin product and an α-enriched whey protein isolate may be increased. Accordingly, the number of additional purification steps necessary to obtain a high value β-lactoglobulin product and a high value α-enriched whey protein isolate may be limited.

Elution of the β-Lactoglobulin Product

According to the teaching of the present invention the method for providing a β-lactoglobulin product and an α-enriched whey protein isolate from whey further comprises the step of:

(v) eluting the β-lactoglobulin product from the chromatographic support using a first elution buffer, said first elution buffer having a pH of 5 or less and a salt concentration of at least 0.1M.

The β-lactoglobulin product is released from the adsorbent by using a first elution buffer, which provides a β-lactoglobulin product with high purity.

In the present context the term "first elution buffer" relates to a liquid used to release the protein(s) adsorbed or fixed to the chromatographic support—i.e. the protein(s) constituting the β-lactoglobulin product.

Suitable first elution buffers may be selected from the group consisting of food grade organic chemicals such as sodium acetate, sodium citrate and sodium lactate.

Using a first elution buffer having a pH of 5 or less and a salt concentration of at least 0.1M the inventors of the present invention surprisingly discovered that a β-lactoglobulin product with high purity could be isolated.

In a combination of preferred embodiments the pH value of the first elution buffer may be 4.5 or less and the salt concentration at the most 0.50 M. Preferably, the pH may be 4.0 or less and the salt concentration at the most 0.60 M. may be 3.5 or less and the salt concentration at the most 0.70 M. Preferably, the pH may be 3.0 or less and the salt concentration at the most 0.80 M. Typically, the pH may be 2.5 or less and the salt concentration at the most 1 M.

The salt concentration in the first elution buffer needed to elute the β-Lactoglobulin product depends on the loading temperature. The higher loading temperature the stronger binding of the proteins to the adsorbent and the more salt may be needed to elute the β-Lactoglobulin product efficiently.

Furthermore the salt concentration and the loading temperature needed to elute the β-Lactoglobulin product also depends on the pH, thus three parameters (salt concentration, temperature and pH) may be adjusted in order to optimize elution of the β-Lactoglobulin product.

The present inventors surprisingly discovered that at least one of the following relations between temperature, pH and salt concentration of the first elution buffer, such as at least two of the following relations, e.g. three of the following relation applies in order to optimize elution of the β-Lactoglobulin product (i) at a substantially constant pH the salt concentration in the first elution buffer should be increased when the temperature is increased in order to optimize elution of the β-Lactoglobulin product and vice versa, (ii) at a substantially constant salt concentration the pH in the first elution buffer should be increased when the temperature is increased and vice versa in order to optimize elution of the β-Lactoglobulin product and (iii) at a substantially constant temperature the salt concentration should be increased when the pH is decreased in the first elution buffer and vice versa in order to optimize elution of the β-Lactoglobulin product.

In an embodiment the loading may be performed at a temperature in the range from 5-25° C., the β-lactoglobulin product is eluted at a pH of 3.5 or less the salt concentration may be in the range from 0.2-0.5M (see example 3).

In another embodiment the loading may be performed at a temperature in the range from 5-10° C., the β-lactoglobulin product is eluted at a pH of 3.5 the salt concentration may be in the range from 0.3-0.4M (see example 2).

In a further embodiment the loading may be performed at a temperature in the range from 18-25° C., the β-lactoglobulin product is eluted at a pH of 3.5 or less the salt concentration in the range from 0.35-0.45M (see example 2).

In yet an embodiment the loading may be performed at a temperature in the range from 40-60° C. and at a pH of 5.0 or less the salt concentration in the range from 0.1-0.7M.

In yet an embodiment the loading may be performed at a temperature in the range from 40-60° C. and at a pH of 4.5 or less the salt concentration in the range from 0.1-0.45M (see example 5).

In yet an embodiment the loading may be performed at a temperature in the range from 40-60° C. and at a pH of 4.0 or less the salt concentration in the range from 0.1-0.50M (see example 5).

In yet an embodiment the loading may be performed at a temperature in the range from 40-60° C. and at a pH of 3.5 or less the salt concentration in the range from 0.35-0.70M (see example 2).

When the elution of the β-Lactoglobulin product may be performed at a pH value of 3.0 or less, such as 2.5, e.g. 2.0 or less the salt concentration in the first elution buffer may be increased.

In a further embodiment the loading may be performed at a temperature in the range from 18-25° C., the β-lactoglobulin product is eluted at a pH of 3.0 or less the salt concentration in the range from 0.40-0.80M (see example 4).

In a further embodiment the loading may be performed at a temperature in the range from 18-25° C., the β-lactoglobulin product is eluted at a pH of 2.5 or less the salt concentration in the range from 0.40-1.0M (see example 4).

Preferred salts may be selected from the group consisting of inorganic salts of food grade such as sodium chloride, potassium chloride, calcium chloride, sodium sulphate and organic salts such as sodium acetate, sodium citrate, sodium lactate.

In a preferred embodiment of the present invention the acids applicable for adjusting the pH value of the first elution buffer may be selected from the group of acids outlined previously for adjusting the pH value of the whey.

The properties of the first elution buffer may be influenced by changing parameters such as pH, ionic strength, salt content, conductivity, hydrophobicity, charge, temperature and pressure. The terms "ionic strength", "salt content" and "conductivity" relates to different expressions of the same parameter i.e. they represent different ways to measure the content of salt. In the present context the term "conductivity" relates to the ability of the first elution buffer to conduct an electrical current. In an embodiment of the present invention the first elution buffer has a conductivity of at least 5 mS/cm, such as at least 10 mS/cm, e.g. at least 20 mS/cm, such as at least 30 mS/cm, e.g. at least 50 mS/cm, such as at least 75 mS/cm, e.g. at least 100 mS/cm, such as at least 125 mS/cm, e.g. at least 150 mS/cm, such as at least 200 mS/cm at 20° C.

In an embodiment of the present invention the first elution buffer further has a temperature in the range from 1-65° C., such as in the range from 5-60° C., e.g. in the range from 10-55° C., such as in the range from 15-50° C., e.g. in the range from 20-45° C., such as in the range from 25-40° C., e.g. in the range from 30-35° C., such as in the range from 5-10° C., e.g. in the range from 40-65° C., such as in the range from 20-35° C., e.g. in the range from 20-30° C. so as to ensure optimal selective elution of the protein(s) constituting the β-lactoglobulin product.

In a preferred embodiment of the present invention the flow rate used for the elution of the β-lactoglobulin product may be selected from the ranges outlined previously for loading the whey to the chromatographic support.

Due to the specific combination of pH and salt concentration of the first elution buffer the amount of β-lactoglobulin in the β-lactoglobulin product obtained in step (v) may be at least 85%, e.g. at least 86%, such as at least 87%, e.g. at least 88%, such as at least 89%, e.g. at least 90%, such as at least 91%, e.g. at least 92%, such as at least 93%, e.g. at least 94%, such as at least 95%, e.g. at least 96%, such as at least 97%, e.g. at least 98%, such as at least 99% relative to the total amount of protein in the β-lactoglobulin product (see example 2).

Thus, in an embodiment of the present invention the amount of β-lactoglobulin in the β-lactoglobulin product obtained in step (v) may be increased by at least 5%, such as at least 10%, e.g. at least 15%, such as at least 20%, e.g. at least 30%, such as at least 40%, e.g. at least 50%, such as at least 60% relative to the total amount of β-lactoglobulin in the whey loaded on to the chromatographic support.

The surprising effect of the specific combination of pH and salt concentration of the first elution buffer may be reflected in the amount of α-lactalbumin present in the isolated β-lactoglobulin product. In an embodiment of the present invention the amount of α-lactalbumin in the β-lactoglobulin product obtained in step (v) may be at the most 5%, such as at the most 4%, e.g. at the most 3%, such as at the most 2%, such as in the range from 2-5%, e.g. in the range from 3-4% relative to the total amount of protein in the β-lactoglobulin product (see example 2).

In an embodiment the amount of immunoglobulin G in the β-lactoglobulin product obtained in step (v) may be at the most 10%, such as at the most 8%, e.g. at the most 6%, such as at the most 4%, e.g. at the most 2%, such as in the range from 2-10%, e.g. in the range from 4-8%, such as in the range from 6-7% relative to the total amount of protein in the β-lactoglobulin product (see example 2).

These low amounts of α-lactalbumin and/or immunoglobulin G in the β-lactoglobulin product are highly surprising. Accordingly, the method disclosed in the present invention simultaneously allows for I. the provision of a high purity β-lactoglobulin product comprising a low amount of α-lactalbumin and/or immunoglobulin G and II. for the provision of a α-enriched whey protein isolate comprising low amounts of β-lactoglobulin and high amounts of α-lactalbumin and immunoglobulin G.

In another embodiment the amount of bovine serum albumin in the β-lactoglobulin product obtained in step (v) may be at the most 2%, such as at the most 1% relative to the total amount of protein in the β-lactoglobulin product. In yet an embodiment the amount of lactoferrin in the β-lactoglobulin product obtained in step (v) may be at the most 2%, such as at the most 1% relative to the total amount of protein in the β-lactoglobulin product. In a further embodiment of the present invention the amount of glycomacropeptide in the β-lactoglobulin product obtained in step (v) may be at the most 2%, such as at the most 1% relative to the total amount of protein in the β-lactoglobulin product. In yet an embodiment of the present invention the amount of carbohydrate in the β-lactoglobulin product obtained in step (v) may be at the most 15%, e.g. at the most 12%, such as at the most 10%, e.g. at the most 8%, such as at the most 6%, e.g. at the most 4%, such as at the most 2%, e.g. in the range from 2-15%, such as in the range from 4-13%, e.g. in the range from 6-11%, such as in the range from 8-10% relative to the total amount of dry matter in the β-lactoglobulin product. In a further embodiment of the present invention the amount of fat in the β-lactoglobulin product obtained in step (v) may be at the most 5%, such as at the most 4%, e.g. at the most 3%, such as at the most 2%, e.g. in the range from 2-5%, such as in the range from 3-4% relative to the total amount of dry matter in the β-lactoglobulin product (see example 2).

In order to increase the productivity (g product produced per time unit) it may be feasible to reload the column with whey after the elution of the β-Lactoglobulin product.

In a preferred embodiment the adsorbent may be washed after the β-Lactoglobulin elution to remove salt and the column reloaded with pH adjusted whey. After reload the adsorbent may be washed followed by β-Lactoglobulin elution.

The reloading step may be performed several times the after β-Lactoglobulin elution before eluting the α-enriched whey protein isolate as disclosed below.

This reloading step may result in a larger amount of produced protein per cycle using a lower buffer consumption and less time [Example 8,9].

Accordingly, the present invention pertains to a method wherein the column is reloaded with pH adjusted whey after the elution of the β-lactoglobulin product in step (v).

Elution of the α-Enriched Whey Protein Isolate

According to the teaching of the present invention the method for providing a β-lactoglobulin product and an α-enriched whey protein isolate from whey further comprises the step of:

(vi) eluting the α-enriched whey protein isolate with a second elution buffer.

The α-enriched whey protein isolate may be released from the adsorbent by using a second elution buffer.

In the present context the term "second elution buffer" relates to a liquid used to release proteins adsorbed or fixed to the chromatographic support—i.e. the proteins constituting the enriched whey protein isolate.

Essentially the α-enriched whey protein isolate consists of the proteins remaining after the elution of the β-lactoglobulin product. In a preferred embodiment of the present invention the α-enriched whey protein isolate may be eluted from the chromatographic support by increasing the pH value and/or by increasing the salt concentration of the second elution buffer.

In a preferred embodiment of the present invention the second elution buffer has a salt concentration of at least 0.05M, such as at least 0.1M, e.g. at least 0.2M, such as at least 0.3M, e.g. at least 0.5M, such as at least 0.65M, e.g. at least 0.7M, such as at least 0.8M, e.g. at least 1M salt.

In a preferred embodiment of the present invention the salts used for adjusting the salt concentration of the second elution buffer may be selected from the group outlined previously of adjusting the salt concentration of the first elution buffer.

Generally, it may be preferred that the salt concentration is kept as low as possible without substantially affecting either the elution efficiency or elution specificity. By using a high salt concentration additional steps may be needed to remove the remaining salt from the isolate—thus, leading to increased production costs.

In a preferred embodiment the second elution buffer comprises a pH value in the range from pH 4-13, e.g. in the range from pH 9-12, such as in the range from pH 10-12, e.g. in the range from pH 10.5-11.5, such as in the range from pH 11.0-12.

Suitable second elution buffers may be selected from the group consisting of sodium hydroxide, potassium hydroxide, calcium hydroxide, ammonium hydroxide, potassium phosphate, sodium phosphate, sodium citrate, sodium acetate, sodium carbonate Common low cost and non-toxic bases are applicable for adjusting the pH value of the second elution buffer. Preferred bases are selected from the group consisting of sodium hydroxide, potassium hydroxide, calcium hydroxide, ammonium hydroxide and any combinations hereof.

In a combination of preferred embodiments the second elution buffer comprises a pH in the range from 4-13 and a salt concentration of at least 0.05M, such as at least 0.1M, e.g. at least 0.2M, such as at least 0.3M, e.g. at least 0.5M, such as at least 0.65M, e.g. at least 0.7M, such as at least 0.8M, e.g. at least 1M salt.

The properties of the second elution buffer may be influenced by changing parameters such as pH, ionic strength, salt content, hydrophobicity, charge, temperature and pressure. These changes may influence the conductivity of the second elution buffer. In the present context the term "conductivity" relates to the ability of the second elution buffer to conduct an electrical current. In an embodiment of the present invention the second elution buffer has a conductivity of at least 5 mS/cm, such as at least 10 mS/cm, e.g. at least 20 mS/cm, such as at least 30 mS/cm, e.g. at least 50 mS/cm, such as at least 75 mS/cm, e.g. at least 100 mS/cm, such as at least 125 mS/cm, e.g. at least 150 mS/cm, such as at least 200 mS/cm at 20° C.

In an embodiment of the present invention the second elution buffer further has a temperature in the range from 1-65° C., such as in the range from 5-60° C., e.g. in the range from 10-55° C., such as in the range from 15-50° C., e.g. in the range from 20-45° C., such as in the range from 25-40° C., e.g. in the range from 30-35° C., such as in the range from 5-10° C., e.g. in the range from 40-65° C., such as in the range from 20-35° C., e.g. in the range from 20-30° C. so as to ensure optimal elution of the remaining proteins i.e. the proteins constituting the α-enriched whey protein isolate.

Due to the surprising elution of β-lactoglobulin product in step (v) and limited amounts of other proteins, the α-enriched whey protein isolate comprises one or more proteins selected from the group consisting of α-lactalbumin, immunoglobulin G, bovine serum albumin and lactoferrin, such as 2 or more, e.g. 3 or more, such as 4 of the proteins.

In an embodiment of the present invention the amount of α-lactalbumin in the α-enriched whey protein isolate obtained in step (vi) may be at least 25%, such as at least 30%, e.g. at least 40%, such as at least 50%, e.g. at least 60% relative to the total amount of protein in the α-enriched whey protein isolate (see example 2).

Thus, in an embodiment of the present invention the amount of α-lactalbumin in the α-enriched whey protein isolate obtained in step (vi) may be increased by at least 5%, such as at least 10%, e.g. at least 15%, such as at least 20%, e.g. at least 30%, such as at least 40%, e.g. at least 50%, such as at least 60% relative to the total amount of α-lactalbumin in the whey loaded on to the chromatographic support.

It may be preferred that the amount of immunoglobulin G in the α-enriched whey protein isolate obtained in step (vi) may be at least 5%, such as at least 7%, e.g. at least 9%, such as at least 11%, e.g. at least 13%, such as at least 15%, e.g. in the range from 5-15%, such as in the range from 7-13%, e.g. in the range from 9-11% relative to the total amount of protein in the α-enriched whey protein isolate. The fact that high amounts of immunoglobulin G may be eluted as part of the α-enriched whey protein isolate is highly surprising, thus adding significant value to the isolated α-enriched whey protein isolate (see example 2).

In an embodiment of the present invention the amount of β-lactoglobulin in the α-enriched whey protein isolate obtained in step (vi) may be less than 25%, e.g. less than 20%, such as less than 19%, e.g. less than 18%, such as less than 17%, e.g. less than 16%, such as less than 15%, e.g. less than 14%, such as less than 13%, e.g. less than 12%, such as less than 11%, e.g. less than 10%, such as less than 9%, e.g. less than 8%, such as less than 7%, e.g. less than 6%, such as less than 5%, e.g. less than 4%, such as less than 3%, e.g. less than 2%, such as less than 1%, e.g. in the range from 1-25%, such as in the range from 3-22%, e.g. in the range from 5-20%, such as in the range from 7-18%, e.g. in the range from 9-13% relative to the total amount of protein in the α-enriched whey protein isolate thus allowing the use of the α-enriched whey protein isolate as an infant formula or as an additive in an infant formula (see example 2).

In an embodiment of the present invention the amount of bovine serum albumin in the α-lactalbumin enriched protein isolate obtained in step (vi) may be at least 10%, such as at least 12%, e.g. at least 14%, e.g. at least 16% relative to the total amount of protein in the α-enriched whey protein isolate. In yet an embodiment of the present invention amount of lactoferrin in the α-enriched whey protein isolate obtained in step (vi) may be at least 1%, such as at least 3%, e.g. at least 5% relative to the total amount of protein in the α-enriched whey protein isolate. In a further embodiment of the present invention the glycomacropeptide content in the α-enriched whey protein isolate obtained in step (vi) may be at the most 2%, such as at the most 1%, relative to the amount of protein in the α-enriched whey protein isolate. In another embodiment of the present invention the carbohydrate content in the α-enriched whey protein isolate obtained in step (vi) may be at the most 10%, such as at the most 8%, e.g. at the most 6%, such as at the most 4%, e.g. at the most 2% relative to the total amount of dry matter in the α-enriched whey protein isolate.

In yet an embodiment of the present invention the fat content in the α-enriched whey protein isolate obtained in step (vi) may be at the most 1% relative to the total amount of dry matter in the α-enriched whey protein isolate (see example 2).

It may be preferred that the eluting performed in step (v) and/or (vi) is/are performed at a temperature in the range from 1-65° C., such as in the range from 5-60° C., e.g. in the range from 10-55° C., such as in the range from 15-50° C., e.g. in the range from 20-45° C., such as in the range from 25-40° C., e.g. in the range from 30-35° C., such as in the range from 5-10° C., e.g. in the range from 40-65° C., such as in the range from 20-35° C., e.g. in the range from 20-30° C. in order to ensure optimal elution conditions when eluting the α-enriched whey protein isolate.

The β-Lactoglobulin Product

The method of the present invention allows for the isolation of a β-lactoglubulin product which may be obtainable by the said method.

In an aspect the present invention further pertains to a β-lactoglubulin product comprising β-lactoglubulin. Preferably, the β-lactoglubulin product comprises β-lactoglubulin in the amount of at least 85%, such as at least 86%, e.g. at least 87%, such as at least 88%, e.g. at least 89%, such as at least 90%, e.g. at least 91%, such as at least 92%, e.g. at least 93%, such as at least 94%, e.g. at least 95%, such as at least 96%, e.g. at least 97%, such as at least 98%, e.g. at least 99%, such as in the range from 85-99%, e.g. in the range from 87-97%, such as in the range from 89-95%, e.g. in the range from 91-93% when compared to the total amount of protein in the β-lactoglubulin product.

The β-lactoglubulin product may further comprise one or more of the proteins selected from the group consisting of, immunoglobulin G, bovine serum albumin, lactoferrin and α-Lactalbumin, such as two or more, e.g. 3 or more components.

It may be presently preferred that the β-lactoglubulin product is high in β-lactoglubulin and low in other proteins. Besides from increasing the value of the β-lactoglubulin product it also increase the value of the α-enriched whey protein isolate.

Accordingly, in a preferred embodiment of the present invention the β-lactoglubulin product comprises α-lactalbumin in the amount of at the most 5%, e.g. at the most 4%, such as at the most 3%, e.g. at the most 2%, such as at the most 1% relative to the total amount of protein in the β-lactoglobulin product.

Thus, in a preferred embodiment of the present invention the β-lactoglubulin comprises immunoglobulin G in the amount of at the most 10%, such as at the most 8%, e.g. at the most 6%, such as at the most 4%, e.g. at the most 2%, such as in the range from 2-10%, e.g. in the range from 4-8%, such as in the range from 6-7% when compared to the total amount of protein in the β-lactoglubulin product.

In a combination of preferred embodiments of the present invention the β-lactoglubulin comprises β-lactoglubulin in the amount of at least 85% and immunoglobulin G in the amount of at the most 10% when compared to the total amount of protein in the β-lactoglubulin product, such as β-lactoglubulin in the amount of at least 90% and immunoglobulin G in the amount of at the most 8% when compared to the total amount of protein in the β-lactoglubulin product, e.g. β-lactoglubulin in the amount of at least 95% and immunoglobulin G in the amount of at the most 6% when compared to the total amount of protein in the β-lactoglubulin product.

In another preferred embodiment of the present invention the β-lactoglubulin product comprises bovine serum albumin in the amount of at the most 2%, such as at the most 1%, when compared to the total amount of protein in the β-lactoglubulin product.

In a further preferred embodiment of the present invention the β-lactoglubulin product comprises lactoferrin in the amount of at the most 2%, such as at the most 1%, when compared to the total amount of protein in the β-lactoglubulin product.

In an embodiment of the present invention the β-lactoglubulin product may be used as a food ingredient. Accordingly, the present invention also pertains to food ingredients and food products comprising the β-lactoglubulin product or the food ingredient previously mentioned.

In order to further increase the value of the β-lactoglubulin product, the present invention also provides a method for purifying the β-lactoglubulin product for obtaining a composition comprising at least 85%, e.g. at least 90% β-lactoglubulin, such as at least 91% β-lactoglubulin, e.g. at least 92% β-lactoglubulin, such as at least 93% β-lactoglubulin, e.g. at least 94% β-lactoglubulin, such as at least 95% β-lactoglubulin, e.g. at least 96% β-lactoglubulin, such as at least 97% β-lactoglubulin, e.g. at least 98% β-lactoglubulin, such as at least 99% β-lactoglubulin when compared to the amount protein in the β-lactoglubulin product.

The α-Enriched Whey Protein Product

The method of the present invention allows for the isolation of an α-enriched whey protein isolate obtainable by the said method.

In an aspect the present invention further pertains to an α-enriched whey protein isolate comprising α-lactalbumin and immunoglobulin G. It is presently preferred that the α-enriched whey protein isolate comprises low amounts of β-lactoglobulin and high amounts of α-lactalbumin and immunoglobulin G.

It may be presently preferred that the α-enriched whey protein isolate comprises a low amount of β-lactoglobulin and high amounts of nutritional valuable proteins.

Thus, in a preferred embodiment of the present invention the α-enriched whey protein isolate comprises α-lactalbumin in the amount of at least 25%, such as at least 30%, e.g. at least 40%, such as at least 50%, e.g. at least 60% relative to the total amount of protein in the α-enriched whey protein isolate.

It may be preferred that the amount of β-lactoglobulin in the α-enriched whey protein isolate is limited due to the intolerance to β-lactoglobulin by many infants Thus, in a preferred embodiment of the present invention the amount of β-lactoglobulin in the α-enriched whey protein isolate may be less than 25%, e.g. less than 20%, such as less than 19%, e.g. less than 18%, such as less than 17%, e.g. less than 16%, such as less than 15%, e.g. less than 14%, such as less than 13%, e.g. less than 12%, such as less than 11%, e.g. less than 10%, such as less than 9%, e.g. less than 8%, such as less than 7%, e.g. less than 6%, such as less than 5%, e.g. less than 4%, such as less than 3%, e.g. less than 2%, such as less than 1% relative to the total amount of protein in the α-enriched whey protein isolate.

Even more preferably, the α-enriched whey protein isolate comprises immunoglobulin G in the amount of at least 5%, e.g. at least 7%, such as at least 9%, e.g. at least 10%, such as in the range from 5-10%, e.g. in the range from 7-9% when compared to the total amount of protein in the α-enriched whey protein isolate.

The α-enriched whey protein isolate may further comprise one or more proteins selected from the group consisting of bovine serum albumin and lactoferrin.

Thus, in a preferred embodiment of the present invention the α-enriched whey protein isolate comprises lactoferrin in the amount of at least 1%, such as at least 3%, e.g. at least 5% when compared to the total amount of protein in the α-enriched whey protein isolate.

In another preferred embodiment of the present invention the α-enriched whey protein isolate comprises bovine serum albumin in the amount of at least 10%, such as at least 12%, e.g. at least 14%, such at least 16%, such as in the range from 10-16%, e.g. in the range from 12-14% when compared to the total amount of protein in the α-enriched whey protein isolate.

In an embodiment of the present invention the α-enriched whey protein isolate may be used as a food ingredient and/or in infant formula.

The combination of low amounts of β-lactoglobulin and high amounts of α-lactalbumin and immunoglobulin G increase the value of the α-enriched whey protein isolate, as it may be used in various food sources such infant formula. As will be apparent to the skilled person the need for additional purification steps are indeed unneeded or limited due to the specific composition of the α-enriched whey protein isolate.

Accordingly, the present invention also pertains to food ingredients, food products and infant formulas comprising the α-enriched whey protein isolate or the previously mentioned food ingredients.

Further Embodiments of the Present Invention

In a further aspect the present invention pertains to a method for improving the isolation of a β-lactoglobulin product and an α-enriched whey protein isolate from whey, the method comprises first elution conditions having the first specific relation between pH, salt concentration and temperature obtaining the β-lactoglobulin product and a second elution condition obtaining the α-enriched whey protein isolate, said first elution condition comprising at least one of the following relations between temperature, pH and salt concentration of the first elution condition, such as at least two of the following relations, e.g. three of the following relation applies in order to optimize elution of the β-Lactoglobulin product (i) at a substantially constant pH the salt concentration in the first elution condition should be increased when the temperature is increased in order to optimize elution of the β-Lactoglobulin product and vice versa, (ii) at a substantially constant salt concentration the pH in the first elution buffer should be increased when the temperature is increased and vice versa in order to optimize elution of the β-Lactoglobulin product and (iii) at a substantially constant temperature the salt concentration should be increased when the pH is decreased in the first elution condition and vice versa in order to optimize elution of the β-Lactoglobulin product.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Raw Material

Bovine sweet whey from mozzarella cheese production with a concentration of α-LA of 0.60 mg/ml, pH 6.2.

Bovine acidic whey from cheese production with a concentration of α-LA of 0.52 mg/ml, pH 4.56.

Pre-Treatment of Raw Material:

For packed bed experiments the sweet whey was clarified by centrifugation and pH is adjusted with hydrochloride acid.

For expanded bed adsorption the sweet whey was pH adjusted with hydrochloric acid.

Example 1

Binding of α-LA as a Function of pH 6 experiments (A-E) were performed where the loading pH was respectively pH 2.5, pH 3.0, pH 3.5, pH 4.0 and pH 4.5.
Adsorbent FastLine®SP cat. no. 1303, UpFront Chromatography A/S. The adsorbent was based on agarose with tungsten carbide particles incorporated, the density of the conglomerate particles was 2.4 g/ml and the particle diameter was in the range of 20-250 μm with a volume mean particle diameter (D (4.3) of 163 μm (as determined on the Mastersizer 2000E, Malvern Instruments, Worcestershire, UK). The adsorbent comprised butansulfonic acid as the ligand and had a ligand concentration of 138 micromoles per ml sedimented adsorbent.
Process Parameters The experiments were performed at room temperature (20-25° C.).

The experiments were performed in packed bed disposable plastic columns from BioRad.

The columns were packed with 1 ml adsorbent.

Experiment A) The adsorbent was equilibrated with 10 ml 10 mM sodium citrate pH 2.5. 20 ml sweet whey pH 2.5 was loaded onto the column. Flow rate 0.2 ml/min.

Experiment B) The adsorbent was equilibrated with 10 ml 10 mM sodium citrate pH 3.0. 20 ml sweet whey pH 3.0 was loaded onto the column. Flow rate 0.2 ml/min.

Experiment C) The adsorbent was equilibrated with 10 ml 10 mM sodium citrate pH 3.5. 20 ml sweet whey pH 3.5 was loaded onto the column. Flow rate 0.2 ml/min.

Experiment D) The adsorbent was equilibrated with 10 ml 10 mM sodium citrate pH 4.0. 20 ml sweet whey pH 4.0 was loaded onto the column. Flow rate 0.2 ml/min.

Experiment E) The adsorbent was equilibrated with 10 ml 10 mM sodium citrate pH 4.5. 20 ml sweet whey pH 4.5 was loaded onto the column. Flow rate 0.2 ml/min.

20 ml of whey correspond to 12 mg α-Lactalbumin loaded per ml adsorbent.

All columns were washed with 10 mM sodium citrate pH 3.5, 5 ml.

The β-Lactoglobulin was eluted with 0.4 M NaCl 50 mM sodium citrate pH 3.5, 10 ml.

The α-Lactalbumin was eluted with 20 mM NaOH, 10 ml. After elution the pH was adjusted to pH 7.0 with 1 M hydrochloric acid.
Results Single Radial Immunodiffusion (SRI) was performed in order to quantify the relative yield in percent of α-Lactalbumin, β-Lactoglobulin, bovine serum albumin, immunoglobulin G and Lactoferrin in the fractions from the column as described in Scand. J. Immunol. Vol. 17, Suppl. 10, 41-56, 1983.

The SRI was performed with: Purified immunoglobulin fraction from hyperimmune rabbit serum raised against bovine α-Lactalbumin produced by UpFront Chromatography A/S (6.5 μl per cm$^2$), purified immunoglobulin fraction from hyperimmune rabbit serum raised against bovine β-Lactoglobulin produced by UpFront Chromatography A/S (21.4 μl per cm$^2$), purified immunoglobulin fraction from hyperimmune rabbit serum raised against bovine serum albumin produced by UpFront Chromatography A/S (5.7 µl per cm²), purified immunoglobulin fraction from hyperimmune rabbit serum raised against bovine lactoferrin produced by UpFront Chromatography A/S (3 µl per cm²), purified immunoglobulin fraction from hyperimmune rabbit serum raised against bovine immunoglobulin G produced by UpFront Chromatography A/S (5 µl per cm²)

A standard curve was performed with the protein solution loaded onto the column in the concentration of 100%, 80%, 60%, 40%, 20% and 10%. Each of the fractions was read relative to the standard curve.

The table below shows the relative yield in percent of the raw material loaded onto the column:

Determination of α-Lactalbumin

| pH | % α-lactalbumin in run-through fraction | % α-lactalbumin in eluate 1 (β-lactoglobulin product) | % α-lactalbumin in eluate 2 (α-enriched whey protein isolate) |
|---|---|---|---|
| 2.5 | 2.5 | 10 | 70 |
| 3.0 | 2.5 | 10 | 75 |
| 3.5 | 7 | 10 | 70 |
| 4.0 | 10 | 10 | 70 |
| 4.5 | 100 | 0 | 0 |

From the results it is concluded that in order to obtain a high binding capacity of α-lactalbumin the pH in the whey shall be adjusted to less than pH 4.5 before loading it onto the column.

Example 2

Production of a β-Lactoglobulin Product and an α-Enriched Whey Protein Isolate at Different Temperatures Three EBA experiments (A-C) were performed at 10° C., 20° C. and 50° C.

Adsorbent

FastLine SP Cat. No. 1303, UpFront Chromatography A/S. See example 1.

Process Parameters

The experiment was performed in a FastLine® 10 expanded bed column (Ø=1 cm) product number 7010-0000, UpFront Chromatography A/S.

The column was packed with 50 cm of adsorbent (40 ml).

Load: 800 ml sweet whey pH 3.5. Corresponds to 12 mg α-Lactalbumin loaded per ml adsorbent.

Flow rate during the entire process 15 cm/min=12 ml/min.

Experiment A, 10° C.

The experiment was performed in a refrigerated room (10° C.).

All buffers and the sweet whey had a temperature of 10° C.

Equilibration and washing buffer: 10 mM sodium citrate pH 3.5.

The β-Lactoglobulin was eluted with 0.35 M NaCl 50 mM sodium citrate pH 3.5.

The α-Lactalbumin was eluted with 20 mM NaOH. After elution the pH was adjusted to pH 7.0 with 1 M hydrochloric acid.

Experiment B, 20° C.=Room Temperature

All buffers and the sweet whey had a temperature of 20-25° C.

Equilibration and washing buffer: 10 mM sodium citrate pH 3.5.

The β-Lactoglobulin was eluted with 0.40 M NaCl 50 mM sodium citrate pH 3.5.

The α-Lactalbumin was eluted with 20 mM NaOH. After elution the pH was adjusted to pH 7.0 with 1 M hydrochloric acid.

Experiment C, 50° C.

The experiment was performed in a heated cupboard (50° C.).

All buffers and the sweet whey were heated up to 50° C. through a heat exchanger right before entering the column.

Equilibration and washing buffer: 10 mM sodium citrate pH 3.5.

The β-Lactoglobulin was eluted with 0.60 M NaCl 5 mM lactic acid pH 3.5.

The α-Lactalbumin was eluted with 20 mM NaOH. After elution the pH was adjusted to pH 7.0 with 1 M hydrochloric acid.

Results

SRI was used to determine the relative yield in percent of the raw material loaded onto the column see example 1:

| | Determination of α-Lactalbumin | | |
|---|---|---|---|
| Temperature | % α-Lactalbumin in run-through fraction | % α-Lactalbumin in eluate 1 (β-lactoglobulin product) | % α-Lactalbumin in eluate 2 (α-enriched whey protein isolate) |
| 10° C. | 7% | 15% | 75% |
| 20° C. | <5% | 10% | >80% |
| 50° C. | <5% | 8% | >80% |

| | Determination of β-Lactoglobulin | | |
|---|---|---|---|
| Temperature | % β-Lactoglobulin in run-through fraction | % β-Lactoglobulin in eluate 1 (β-lactoglobulin product) | % β-Lactoglobulin in eluate 2 (α-enriched whey protein isolate) |
| 10° C. | 10% | 80% | 10% |
| 20° C. | <5% | 85-90% | 10% |
| 50° C. | 5-10% | 80% | 5% |

From the results it is concluded that when the elution of the β-lactoglobulin product is performed at pH 3.5 then the salt concentration needed to achieve a high yield of the β-lactoglobulin increases when the loading temperature increases due to a stronger binding of the proteins at high temperatures.

The tables below shows the relative yield in percent of the raw material loaded onto the three columns for the following proteins:

IgG, Lactoferrin, bovine serum albumin (BSA), GMP, β-Lactoglobulin and α-Lactalbumin. The tables also show the amount of each of the proteins relative to the total amount of protein in run-through fraction, the β-lactoglobulin product and α-Lactalbumin enriched protein isolate product respectively.

The numbers are based on the following concentrations of the different proteins in the whey:

| Protein | mg/ml | % of total amount of protein |
|---|---|---|
| IgG | 0.5 | 9% |
| LF | 0.08 | 1% |
| BSA | 0.3 | 5% |
| GMP | 1.5 | 26% |
| β-Lactoglobulin | 2.8 | 48% |
| α-Lactalbumin | 0.6 | 10% |
| Total | 5.78 | 100% |

| Kold process, 10° C. | | | | | | |
|---|---|---|---|---|---|---|
| Protein | Run-through fraction | % of total amount of protein | β-lacto-globulin product | % of total amount of protein | α-enriched whey protein isolate | % of total amount of protein |
| IgG | 40% | 9.8% | 30% | 6% | 30% | 12.3% |
| LF | 0% | 0% | 0% | 0% | 100% | 6.6% |
| BSA | 5% | 0.7% | 0% | 0% | 95% | 23.8% |
| GMP | 100% | 73.5% | 0% | 0% | 0% | 0% |
| β-Lacto-globulin | 10% | 13.7% | 80% | 90% | 10% | 23.0% |
| α-Lactalbumin | 7% | 2.1% | 15% | 3.6% | 70% | 34.4% |

| Room temperature process. 20-25° C. | | | | | | |
|---|---|---|---|---|---|---|
| Protein | Run-through fraction | % of total amount of protein | β-lactoglobulin product | % of total amount of protein | α-enriched whey protein isolate | % of total amount of protein |
| IgG | 50% | 13.5% | 10% | 2.0% | 40% | 14.7% |
| LF | 0% | 0% | 0% | 0% | 100% | 5.9% |
| BSA | 5% | 0.8% | 0% | 0% | 95% | 21.3% |
| GMP | 100% | 81.1% | 0% | 0% | 0% | 0% |
| beta | 2.5% | 3.8% | 85% | 95.6% | 10% | 20.6% |
| alfa | 2.5% | 0.8% | 10% | 2.4% | 85% | 37.5% |

| Warm proces. 50° C. | | | | | | |
|---|---|---|---|---|---|---|
| Protein | Run-through fraction | % of total amount of protein | β-lacto-globulin product | % of total amount of protein | α-enriched whey protein isolate | % of total amount of protein |
| IgG | 50% | 13.2% | 0% | 0% | 50% | 20.5% |
| LF | 0% | 0% | 0% | 0% | 100% | 6.6% |
| BSA | 20% | 3.2% | 0% | 0% | 80% | 19.7% |
| GMP | 100% | 78.9% | 0% | 0% | 0% | 0% |
| beta | 2.5% | 3.7% | 85% | 97.1% | 5% | 11.5% |
| alfa | 2.5% | 0.8% | 12% | 2.9% | 85% | 41.8% |

From the results it is concluded that the process results in a highly purified β-lactoglobulin product ≥90% of the protein in the β-lactoglobulin product is β-lactoglobulin. The β-lactoglobulin product has a low content of immunoglobulin G (less than 10% of the total protein content).

The higher load temperature the stronger binding of the proteins resulting in a β-lactoglobulin product without other protein contaminants than α-lactalbumin when loading at 50° C.

The α-enriched whey protein isolate has a high concentration of α-lactalbumin >30% of the total protein content and a low content of β-lactoglobulin (less than 25% of the total protein content). More than 10% of the total protein is immunoglobulin G.

Example 3

Production of a β-Lactoglobulin Product and an α-Enriched Whey Protein Isolate where β-Lactoglobulin is Eluted at Different Elution pH-Values Two packed bed experiments were performed (A-B) where the β-Lactoglobulin product was eluted at pH 3.5 respectively 4.0. The experiments were performed at room temperature.

Adsorbent

FastLine®SP Cat. No. 1303, UpFront Chromatography A/S. See example 1.

Process Parameters

The experiments were performed at room temperature (20-25° C.).

The experiments were performed in packed bed disposable plastic columns from BioRad.

The columns were packed with 1 ml adsorbent.

Flow rate during the entire experiment was 0.2 ml/min.

The adsorbents were equilibrated with 10 mM sodium citrate pH 3.5, ml.

20 ml sweet whey pH 3.5 was loaded onto each column—corresponds to 12 mg α-Lactalbumin loaded per ml adsorbent.

Each column was washed with 10 mM sodium citrate pH 3.5, 5 ml.

Column A, β-Lactoglobulin Elution:

0.15 M NaCl 50 mM sodium citrate pH 3.5, 10 ml 0.30 M NaCl 50 mM sodium citrate pH 3.5, 10 ml 0.40 M NaCl 50 mM sodium citrate pH 3.5, 10 ml Column B, β-Lactoglobulin Elution:

0.15 M NaCl 50 mM sodium citrate pH 4.0, 10 ml 0.30 M NaCl 50 mM sodium citrate pH 4.0, 10 ml 0.40 M NaCl 50 mM sodium citrate pH 4.0, 10 ml Elution of α-Enriched Whey Protein Isolate for Both Experiments:

20 mM NaOH, 10 ml. After elution the pH was adjusted to pH 7.0 with 1 M hydrochloric acid.

Results

Single Radial Immunodiffusion (SRI) was performed in order to quantify the relative yield in percent of α-Lactalbumin and β-Lactoglobulin in the fractions from the column. See example 1.

| | Elution of a β-lactoglobulin product at pH 3.5 | | Elution of a β-lactoglobulin product at pH 4.0 | |
|---|---|---|---|---|
| Fraction | % α-Lactalbumin | % β-Lactoglobulin | % α-Lactalbumin | % β-Lactoglobulin |
| Run-through | <5% | 10% | <5% | 10% |
| β-Lactoglobulin elution: | | | | |
| 0.15M NaCl | 0% | 20% | 10% | 30-40% |
| 0.30M NaCl | 5% | 40-50% | 20% | 40-50% |

-continued

| Fraction | Elution of a β-lactoglobulin product at pH 3.5 | | Elution of a β-lactoglobulin product at pH 4.0 | |
|---|---|---|---|---|
| | % α-Lactalbumin | % β-Lactoglobulin | % α-Lactalbumin | % β-Lactoglobulin |
| 0.40M NaCl | 7.5% | 20% | 12.5% | 5% |
| α-enriched whey protein isolate elution | >80% | <5% | 50% | <5% |

From the results it is concluded that when the loading of the when is performed at room temperature it is feasible to separately elute the β-lactoglobulin product at pH 3.5 with salt concentration of 0.4 M NaCl and achieve a high yield of α-lactalbumin in the α-enriched whey protein isolate elution. Elution of the β-lactoglobulin product at pH 4.0 is feasible but the selectivity is low resulting in a low yield of α-lactalbumin in the α-enriched whey protein isolate elution.

Example 4

Production of a β-Lactoglobulin Product and an α-Enriched Whey Protein Isolate at Different Elution pH-Values Two packed bed experiments were performed (A-B) where the β-Lactoglobulin product was eluted at pH 2.5 respectively 3.0. The experiments were performed at room temperature.

Adsorbent
  FastLine®SP Cat. No. 1303, UpFront Chromatography A/S. See example 1.
Process Parameters
  The experiments were performed at room temperature (20-25° C.).
  The experiments were performed in packed bed disposable plastic columns from BioRad.
  The columns were packed with 1 ml adsorbent.
  Flow rate during the entire experiment was 0.2 ml/min.
  The adsorbents were equilibrated with 10 mM sodium citrate pH 3.5, 10 ml.
  20 ml sweet whey pH 3.5 was loaded onto each column. Corresponds to 12 mg α-Lactalbumin loaded per ml adsorbent.
  Column A was washed with 50 mM sodium citrate pH 3.0, 5 ml.
  Column B was washed with 50 mM sodium citrate pH 2.5, 5 ml.
Column A, β-Lactoglobulin Elution:
  0.40 M NaCl 50 mM sodium citrate pH 3.0, 10 ml
  0.60 M NaCl 50 mM sodium citrate pH 3.0, 10 ml
  0.80 M NaCl 50 mM sodium citrate pH 3.0, 10 ml
  1.00 M NaCl 50 mM sodium citrate pH 3.0, 10 ml
Column B, β-Lactoglobulin Elution:
  0.40 M NaCl 50 mM sodium citrate pH 2.5, 10 ml
  0.60 M NaCl 50 mM sodium citrate pH 2.5, 10 ml
  0.80 M NaCl 50 mM sodium citrate pH 2.5, 10 ml
  1.00 M NaCl 50 mM sodium citrate pH 2.5, 10 ml
Elution of α-Enriched Whey Protein Isolate for Both Experiments:
  20 mM NaOH, 10 ml. After elution the pH was adjusted to pH 7.0 with 1 M hydrochloric acid.
Results Single Radial Immunodiffusion (SRI) was performed in order to quantify the relative yield in percent of α-Lactalbumin in the fractions from the column. See example 1. The relative yield of β-Lactoglobulin in the different fractions was estimated by SDS-PAGE.

| Fraction | Elution of a β-lactoglobulin product at pH 3.0 | | Elution of a β-lactoglobulin product at pH 2.5 | |
|---|---|---|---|---|
| | % α-Lactalbumin | % β-Lactoglobulin | % α-Lactalbumin | % β-Lactoglobulin |
| Run-through | <5% | 10% | <5% | 10% |
| β-Lactoglobulin elution: | | | | |
| 0.40M NaCl | 2.5% | 60% | 2.5% | 30% |
| 0.60M NaCl | 5% | 40% | 5% | 50% |
| 0.80M NaCl | 2.5-5% | <5% | 5% | 5-10% |
| 1.00M NaCl | 2.5-5% | 0% | 5% | 0% |
| α-enriched whey protein isolate elution | 70% | <5% | 70% | <5% |

The results show that the lower pH applied for the elution of β-lactoglobulin product the higher salt concentration is needed to achieve a high yield of β-lactoglobulin in the β-lactoglobulin product and still achieve a high yield of α-lactalbumin in the α-enriched whey protein isolate elution.

Example 5

β-Lactoglobulin elution at pH 4.0 and 4.5 at 50° C.
Two EBA experiments were performed (A and B) at 50° C. where the β-Lactoglobulin product was eluted at pH 4.0 and 4.5 respectively.
Adsorbent
  FastLine®SP Cat. No. 1303, UpFront Chromatography A/S. See example 1.
Process Parameters
  The experiment was performed in a FastLine®10 expanded bed column (Ø=1 cm) product number 7010-0000, UpFront Chromatography A/S.
  The column was packed with 75 cm of adsorbent (59 ml).

Load: 2355 ml sweet whey pH 3.5. Corresponds to 24 mg α-Lactalbumin loaded per ml adsorbent.
Flow rate during the entire process 20 cm/min=15 ml/min.
The experiment was performed in a heated cupboard (50° C.).
All buffers and the sweet whey were heated up to 50° C. through a heat exchanger right before entering the column.
Equilibration and washing buffer: 50 mM lactic acid pH 3.5.
Column A, β-Lactoglobulin Elution:
0.2 M NaCl+5 mM sodium citrate pH 4.0
0.3 M NaCl+5 mM sodium citrate pH 4.0
0.4 M NaCl+5 mM sodium citrate pH 4.0
0.5 M NaCl+5 mM sodium citrate pH 4.0
Column B, β-Lactoglobulin Elution:
0.2 M NaCl+5 mM sodium citrate pH 4.5
0.3 M NaCl+5 mM sodium citrate pH 4.5
0.4 M NaCl+5 mM sodium citrate pH 4.5
0.5 M NaCl+5 mM sodium citrate pH 4.5
Elution of α-Enriched Whey Protein Isolate for Both Experiments:
20 mM NaOH. After elution the pH was adjusted to pH 7.0 with 1 M hydrochloric acid.

Results

SRI was used to determine the relative yield in percent of the raw material loaded onto the column see example 1: Determination of α-Lactalbumin and β-Lactoglobulin:

| Fraction | Elution of a β-lactoglobulin product at pH 4.0 | | Elution of a β-lactoglobulin product at pH 4.5 | |
|---|---|---|---|---|
| | % α-lactalbumin | % β-lactoglobulin | % α-lactalbumin | % β-lactoglobulin |
| Run-through | <5% | 35% | <5% | 35% |
| β-lactoglobulin elution: | | | | |
| 0.20M NaCl | 0% | 5% | 0% | 5% |
| 0.30M NaCl | 0% | 20% | 0% | 25% |
| 0.40M NaCl | 0% | 30% | 10% | 30% |
| 0.50M NaCl | <5% | 15% | <5% | <5% |
| α-enriched whey protein isolate elution | 80% | <<5% | 70% | <<5% |

The results show that when the loading temperature is 50° C. the proteins bind stronger and it is therefore feasible to elute the β-lactoglobulin at pH 4.0 and 4.5 and still achieve a high yield of α-lactalbumin in the α-enriched whey protein isolate elution. The higher pH used for the β-lactoglobulin elution the lower concentration of salt is needed to perform the selective elution.

Example 6

α-Lactalbumin Binding Capacity as a Function of Ligand Concentrations

Three experiments (A-C) were performed where three different FastLine SP adsorbents were tested. The ligand concentration was respectively 42, 60, 76, 90 and 138 mmol/L sedimented bed.
Process Parameters
The experiments were performed at room temperature (20-25° C.).
The experiments were performed in packed bed disposable plastic columns from BioRad.
The columns were packed with 1 ml adsorbent.
Flow rate during the entire experiment was 0.2 ml/min.
The adsorbents were equilibrated with 10 mM sodium citrate pH 3.5, 10 ml.
20 ml sweet whey pH 3.5 was loaded onto each column. Corresponds to 12 mg α-Lactalbumin loaded per ml adsorbent.
Each column was washed with 10 mM sodium citrate pH 3.5, 5 ml.
The proteins were eluted with 20 mM NaOH, 10 ml Results The amount of α-Lactalbumin recovered in the run-through and elution fraction was estimated by SDSPAGE gel electroforesis. The results are percentage relative to the total amount of α-Lactalbumin loaded onto the column.

| Ligand concentration, mmol/L | % α-lactalbumin in run-through fraction | % α-lactalbumin in elution fraction |
|---|---|---|
| 42 | 50 | 50 |
| 60 | 20 | 80 |
| 76 | 10 | 90 |
| 90 | <5 | >95 |
| 138 | <5 | >95 |

From the results it is concluded that in order to achieve a satisfactory binding capacity of α-lactalbumin an adsorbent with a ligand concentration of 76 mmol/L or more is needed.

Example 7

Production of a β-Lactoglobulin Product and an α-Enriched Whey Protein Isolate from Acidic Whey at 50° C. EBA Adsorbent
FastLine SP Cat. No. 1303, UpFront Chromatography A/S. See example 1.
Process Parameters
The experiment was performed in a FastLine®10 expanded bed column (Ø=1 cm) product number 7010-0000, UpFront Chromatography A/S.
The column was packed with 50 cm of adsorbent (40 ml).
Flow rate during the entire process 15 cm/min=12 ml/min.
Load: 800 ml acidic whey. Corresponds to 10.4 mg α-Lactalbumin loaded per ml adsorbent.
Process temperature: 50° C.
The experiment was performed in a heated cupboard (50° C.).
All buffers and the sweet whey were heated up to 50° C. through a heat exchanger right before entering the column.

Equilibration and washing buffer: 50 mM lactic acid pH 3.5.

The β-Lactoglobulin was eluted with 0.65 M NaCl 5 mM lactic acid pH 3.5.

The α-Lactalbumin was eluted with 20 mM NaOH.

After elution the pH was adjusted to pH 7.0 with 1 M hydrochloric acid.

Results

Single Radial Immunodiffusion (SRI) was performed in order to quantify the relative yield in percent of α-Lactalbumin in the fractions from the column. See example 1.

The table below shows the relative yield in percent of the raw material loaded onto the column:

Determination of α-Lactalbumin and β-Lactoglobulin

| Fraction | Elution of β-lactoglobulin at pH 4.0 | |
|---|---|---|
| | % α-lactalbumin | % β-lactoglobulin |
| Run-through | <5% | <5% |
| β-lactoglobulin elution: | 5-10% | 90% |
| α-enriched whey protein isolate elution | 80% | 5-10% |

From the results it is concluded that bovine acidic whey is a suitable raw material for the production of production of a β-lactoglobulin product and an α-enriched whey protein isolate Example 8

Production of an α-Enriched Whey Protein Isolate and a β-Lactoglobulin Product with Two β-Lactoglobulin Elutions and Two Times Whey Loading Before the α-Lactalbumin Enriched Protein Isolate is Eluted The experiment was performed as a packed bed experiment performed at room temperature.

Adsorbent

FastLine®SP Cat. No. 1303, UpFront Chromatography A/S. See example 1.

Process Parameters

The experiment was performed at room temperature (20-25° C.).

The experiment was performed in a packed bed disposable plastic column from BioRad.

The column was packed with 1 ml adsorbent.

Flow rate during the entire experiment was 0.2 ml/min.

The adsorbent was equilibrated with 10 mM sodium citrate pH 3.5, 10 ml.

20 ml sweet whey pH 3.5 was loaded (load 1) onto the column—corresponds to 12 mg α-Lactalbumin loaded per ml adsorbent.

The column was washed with 10 mM sodium citrate pH 3.5, 5 ml.

β-Lactoglobulin Elution 1:

0.40 M NaCl 50 mM sodium citrate pH 3.5, 10 ml.

The adsorbent was washed with 10 mM sodium citrate pH 3.5, 5 ml to wash out the elution salt.

20 ml sweet whey pH 3.5 was loaded (load 2) onto the column. Corresponds to 12 mg α-Lactalbumin loaded per ml adsorbent. The column was washed with 10 mM sodium citrate pH 3.5, 5 ml.

β-Lactoglobulin Elution 2:

0.40 M NaCl 50 mM sodium citrate pH 3.5, 10 ml.

Elution of an α-Enriched Whey Protein Isolate:

20 mM NaOH, 10 ml. After elution the pH was adjusted to pH 7.0 with 1 M hydrochloric acid.

Results

Single Radial Immunodiffusion (SRI) was performed in order to quantify the relative yield in percent of α-Lactalbumin and β-Lactoglobulin in the fractions from the column. See example 1.

| Fraction | % α-lactalbumin | % β-lactoglobulin |
|---|---|---|
| Run-through fraction 1 | 5% | 10% |
| Wash 1 | 0% | 0% |
| β-Lactoglobulin elution 1 | 10% | 40% |
| Run-through fraction 2 | 5-10% | 10% |
| Wash 2 | 0% | 0% |
| β-Lactoglobulin elution 2 | 0% | 40% |
| α-enriched whey protein isolate | 75-80% | <<5% |

The results show that it is feasible to load 40 L whey per liter of adsorbent when the load volume is divided into two loads with an elution of the β-lactoglobulin product in between the two loads and still achieve a high yield of both β-lactoglobulin and α-lactalbumin which leads to an overall increase in productivity (see example 9).

Example 9

Productivity of α-Lactalbumin and β-Lactoglobulin at Different Load Ratios

The table below shows the time consumed during the different steps in the process with four different load scenarios:
1) Load ratio 1:20 (20 L sweet whey per L of adsorbent)
2) Load ratio 1:40
3) Load ratio 1:20, after elution of β-Lactoglobulin the adsorbent was loaded one more time load ratio 1:20.
4) Load ratio 1:20 run the experiment two times.

| Step in process | 1:20 | 1:40 | Two time load an β-lactoglobulin elution before α-lactalbumin elution | 1:20 two times |
|---|---|---|---|---|
| Equilibration | 17 min | 17 min | 17 min | 34 min |
| Load | 67 min | 133 min | 67 min | 133 min |
| Wash | 8 min | 8 min | 8 min | 16 min |
| β-lactoglobulin elution | 22 min | 22 min | 22 min | 44 min |
| Wash | — | — | 3 min | — |
| Load 2 | — | — | 67 min | — |
| Wash | — | — | 8 min | — |

-continued

| Step in process | 1:20 | 1:40 | Two time load an β-lactoglobulin elution before α-lactalbumin elution | 1:20 two times |
|---|---|---|---|---|
| β-lactoglobulin elution 2 | — | — | 22 min | — |
| α-lactalbumin elution | 25 min | 25 min | 25 min | 50 min |
| Regeneration | 14 min | 14 min | 14 min | 28 min |
| Total process time | 153 min/ 2.55 hrs | 220 min/ 3.67 hrs | 253 min/ 3.67 hrs | 306 min/ 5.1 hrs |

Results

Single Radial Immunodiffusion (SRI) was performed in order to quantify the relative yield in percent of α-Lactalbumin and β-Lactoglobulin in the fractions from the column. See example 1.

| Process | % β-lactoglobulin in β-lactoglobulin elution | % α-Lactalbumin in α-enriched whey protein isolate |
|---|---|---|
| 1:20 | 80 | 80 |
| 1:40 | 40 | 80 |
| Two times load and β-Lactoglobulin elution before α-Lactalbumin elution (1:40) | 80 | 80 |
| 1:20 two times | 80 | 80 |

With a β-Lactoglobulin concentration of app. 2.8 g/L and a α-Lactalbumin concentration of 0.6 g/L the table below shows the productivity of α-Lactalbumin and β-Lactoglobulin/L loaded whey/hr.

| Process | Productivity g α-lactalbumin and β-lactoglobulin/L loaded whey/hr |
|---|---|
| 1:20 | 1.07 |
| 1:40 | 0.87 |
| Two times load and β-lactoglobulin elution before α-lactalbumin elution (1:40) | 1.29 |
| 1:20 two times | 1.07 |

From the results it is concluded that the productivity (produced g α-lactalbumin and β-lactoglobulin/L loaded whey/hr) is increased with approximately 50% when the load ratio 1:40 divided into two loads with two times elution of the 13-lactoglobulin product before elution of the α-enriched whey protein isolate instead of loading 1:40 in one load with one elution of β-lactoglobulin.

Example 10

Production of a β-Lactoglobulin Product and an α-Enriched Whey Protein Isolate at Different Temperatures at a Flow Rate of 20 cm/min Two EBA experiments (A and B) were performed at 20° C. and 40° C.

Adsorbent

FastLine SP Cat. No. 1303, UpFront Chromatography A/S. See example 1.

Process Parameters

The experiment was performed in a FastLine®10 expanded bed column (Ø=1 cm) product number 7010-0000, UpFront Chromatography A/S.

The column was packed with 75 cm of adsorbent (59 ml).

Load: 2355 ml sweet whey pH 3.5. Corresponds to 24 mg α-Lactalbumin loaded per ml adsorbent.

Flow rate during the entire process 20 cm/min=16 ml/min.

Experiment A, 20° C.=Room Temperature

All buffers and the sweet whey had a temperature of 20-25° C.

Equilibration and washing buffer: 50 mM lactic acid pH 3.5.

The β-Lactoglobulin was eluted with 0.40 M NaCl 5 mM lactic acid pH 3.5.

The α-Lactalbumin was eluted with 20 mM NaOH. After elution the pH was adjusted to pH 7.0 with 1 M hydrochloric acid.

Experiment B, 40° C.

The experiment was performed in a heated cupboard (40° C.).

All buffers and the sweet whey were heated up to 40° C. through a heat exchanger right before entering the column.

Equilibration and washing buffer: 50 mM lactic acid pH 3.5.

The β-Lactoglobulin was eluted with 0.60 M NaCl 5 mM lactic acid pH 3.5.

The α-Lactalbumin was eluted with 20 mM NaOH. After elution the pH was adjusted to pH 7.0 with 1 M hydrochloric acid.

Results

Figure 1:
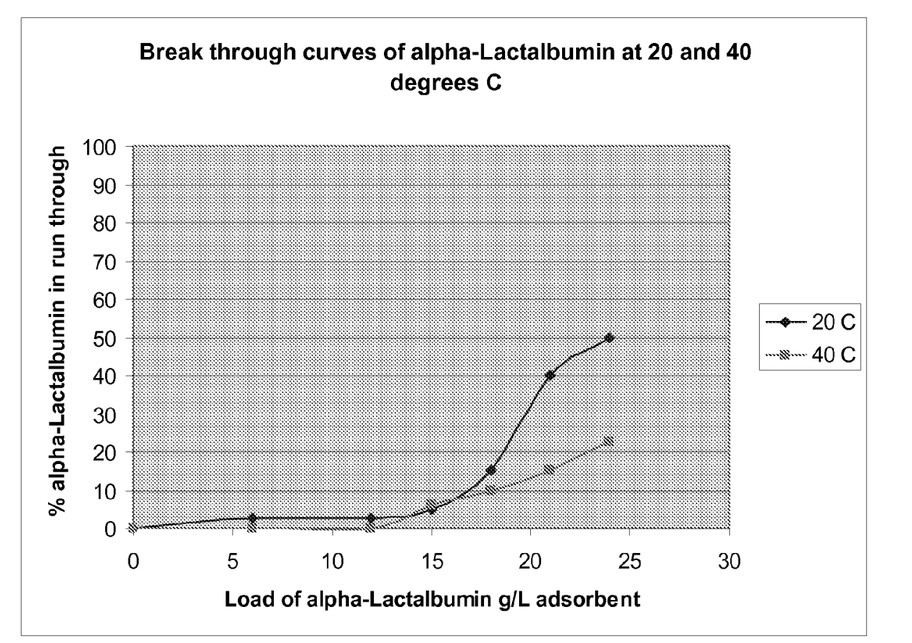
FIG. 1 shows the breakthrough curves for α-lactalbumin from EBA experiments performed at 20° C. and 40° C. Single Radial Immunodiffusion (SRI) was performed in order to quantify the relative yield in percent of α-Lactalbumin in the run through fractions during lod of the whey. The FIGURE shows the break through curve for 40° C. is less steep than for 20° C. meaning that it is possible to bind more α-lactalbumin to the adsorbent at 40° C. than at 20° C.

Single Radial Immunodiffusion (SRI) was performed in order to quantify the relative yield in percent of α-Lactalbumin in the run-through fractions (FIG. 1).

FIG. 1 shows the breakthrough curves for α-lactalbumin from EBA experiments performed at 20° C. and 40° C. Single Radial Immunodiffusion (SRI) was performed in order to quantify the relative yield in percent of α-Lactalbumin in the run through fractions during lod of the whey. The FIGURE shows the break through curve for 40° C. is less steep than for 20° C. meaning that it is possible to bind more α-lactalbumin to the adsorbent at 40° C. than at 20° C.

Example 11

Production of a β-Lactoglobulin Product and an α-Enriched Whey Protein Isolate with CM Cation Exchanger at Room Temperature Adsorbent FastLine®CM, UpFront Chromatography A/S. The adsorbent was based on agarose with tungsten carbide particles incorporated, the density of the conglomerate particles was 2.4 g/ml and the particle diameter was in the range of 20-250 μm with a volume mean particle diameter (D (4.3) of 145 μm (as determined on the Mastersizer 2000E, Malvern Instruments, Worcestershire, UK). The adsorbent comprised chloroacetic acid as the ligand and had a ligand concentration of 146 micromoles per ml sedimented adsorbent.

Process Parameters

The experiment was performed at room temperature (20-25° C.).

The experiment was performed in packed bed disposable plastic columns from BioRad.

The column was packed with 1 ml adsorbent.

The adsorbent was equilibrated with 10 ml 10 mM sodium citrate pH 3.5.

20 ml sweet whey pH 3.5 was loaded onto the column.

Flow rate 0.2 ml/min.

20 ml of whey correspond to 12 mg α-Lactalbumin loaded per ml adsorbent.

The column was washed with 10 mM sodium citrate pH 3.5, 5 ml

The β-Lactoglobulin was eluted with 0.4 M NaCl 50 mM sodium citrate pH 3.5, 10 ml The α-Lactalbumin was eluted with 20 mM NaOH, 10 ml. After elution the pH was adjusted to pH 7.0 with 1 M hydrochloric acid.

Results

SRI was used to determine the relative yield in percent of the raw material loaded onto the column see example 1: Determination of α-Lactalbumin and β-Lactoglobulin:

| Fraction | % α-lactalbumin | % β-lactoglobulin |
|---|---|---|
| Run-through | 50% | 30% |
| β-Lactoglobulin elution: | <5% | 70% |
| α-enriched whey protein isolate elution | 40% | <<5% |

From the results it is concluded that the chloroacetic acid ligand results in a α-enriched whey protein isolate with a low content of β-lactoglobulin.

REFERENCES

EP 0 538 350
Hermanson et al. 1992
U.S. Pat. No. 5,756,680
WO 92/00799
WO 92/18237
WO 92/00799
WO 97/17132
WO 98/33572
WO 00/57982

The invention claimed is:

1. A method for providing a β-lactoglobulin product and an α-enriched whey protein isolate from whey, the method comprises the steps of:
(i) providing whey obtained from an animal,
(ii) adjusting the pH value of the whey to pH 4.5 or below,
(iii) loading the whey to an expanded bed adsorption chromatographic support, said chromatographic support comprising an expanded bed adsorption chromatography adsorbent, said expanded bed adsorption chromatography adsorbent comprising sulfonic acid ligands in a concentration of at least 50 mmol/L adsorbent,
(iv) optionally washing the expanded bed adsorption chromatographic support using a wash buffer and obtaining a wash fraction,
(v) eluting the β-lactoglobulin product from the expanded bed adsorption chromatographic support using a first elution buffer, said first elution buffer having a pH of 5 or less and a salt concentration of at least 0.1M and
(vi) eluting the α-enriched whey protein isolate with a second elution buffer.

2. A method according to claim 1, wherein the loading ratio of the whey is at least 12 g protein/L adsorbent.

3. A method according to claim 1, wherein the first elution buffer has a conductivity of at least 5 mS/cm at 20° C.

4. A method according to claim 1, wherein the amount of immunoglobulin G in the β-lactoglobulin product obtained in step (v) is at the most 10 relative to the total amount of protein in the β-lactoglobulin product.

5. A method according to claim 1, wherein the α-enriched whey protein isolate is eluted from the chromatographic support by increasing the pH value and/or by increasing the salt concentration of the second elution buffer.

6. A method according to claim 1, wherein the second elution buffer has a conductivity of at least 5 mS/cm at 20° C. or wherein the second elution buffer comprises a pH in the range from pH 4-13.

7. A method for providing a β-lactoglobulin product and an α-enriched whey protein isolate from whey, the method comprises the steps of:
(i) providing whey obtained from an animal,
(ii) adjusting the pH value of the whey to pH 4.5 or below,
(iii) loading the whey to an expanded bed adsorption chromatographic support, said chromatographic support comprising an expanded bed adsorption chromatography adsorbent, said expanded bed adsorption chromatography adsorbent comprising sulfonic acid ligands in a concentration of at least 50 mmol/L adsorbent; such that the loading ratio of the whey is at least 10 g α-lactalbumin/L adsorbent, and such that at least 70% of the proteins present in the whey, except for glycomacropeptide, are adsorbed on the chromatographic support,
(iv) optionally washing the expanded bed adsorption chromatographic support using wash buffer and obtaining a wash fraction,
(v) eluting the β-lactoglobulin product from the expanded bed adsorption chromatographic support using a first elution buffer, said first elution buffer having a pH of 5 or less and a salt concentration of at least 0.1M and
(vi) eluting the α-enriched whey protein isolate with a second elution buffer.

* * * * *